(12) United States Patent
Escames Rosa et al.

(10) Patent No.: US 11,234,964 B2
(45) Date of Patent: Feb. 1, 2022

(54) USE OF MELATONIN FOR THE TREATMENT OF TUMORS

(71) Applicant: UNIVERSIDAD DE GRANADA, Granada (ES)

(72) Inventors: Germaine Escames Rosa, Granada (ES); Darío Acuña Castroviejo, Granada (ES); Ana Guerra-Librero Rite, Granada (ES); Beatriz Irene Fernández Gil, Granada (ES); Javier Florido Ruiz, Granada (ES)

(73) Assignee: Universidad De Granada, Granada (ES)

( * ) Notice: Subject to any disclaimer, the term of this patent is extended or adjusted under 35 U.S.C. 154(b) by 0 days.

(21) Appl. No.: 16/498,825

(22) PCT Filed: Apr. 2, 2018

(86) PCT No.: PCT/ES2018/070289
§ 371 (c)(1),
(2) Date: Sep. 27, 2019

(87) PCT Pub. No.: WO2018/178497
PCT Pub. Date: Oct. 4, 2018

(65) Prior Publication Data
US 2021/0106562 A1    Apr. 15, 2021

(30) Foreign Application Priority Data

Mar. 31, 2017 (ES) .............................. ES201730598

(51) Int. Cl.
| | |
|---|---|
| *A61K 31/4045* | (2006.01) |
| *A61P 35/00* | (2006.01) |
| *A61K 9/00* | (2006.01) |
| *A61K 45/06* | (2006.01) |

(52) U.S. Cl.
CPC ........ *A61K 31/4045* (2013.01); *A61K 9/0019* (2013.01); *A61K 45/06* (2013.01); *A61P 35/00* (2018.01)

(58) Field of Classification Search
CPC ................................................ A61K 31/4045
See application file for complete search history.

(56) References Cited

U.S. PATENT DOCUMENTS

| | | | | |
|---|---|---|---|---|
| 8,075,902 | B2 * | 12/2011 | Powell | A61K 31/4965 424/198.1 |
| 8,962,673 | B2 * | 2/2015 | Escames Rosa | A61P 1/02 514/415 |
| 10,092,544 | B2 * | 10/2018 | Escames Rosa | A61K 8/35 |
| 2014/0329785 | A1 | 11/2014 | Wong et al. | |

OTHER PUBLICATIONS

Hong, Y. et al, "Melatonin treatment induces interplay of apoptosis, autophagy, and senescence in human colorectal cancer cells", Journal of Pineal Research, 2014, vol. 56, pp. 264-274.
Park, S. et al., "Melatonin suppresses tumor angiogenesis by inhibiting HIF-1α stabilization under hypoxia", Journal of Pineal Research, 2010, vol. 48, pp. 178-184.
Trubiani, O. et al., "Melatonin provokes cell death in human B-lymphoma cells by mitochondrial-dependent apoptotic pathway activation", Journal of Pineal Research, 2005, vol. 39, pp. 425-431.
International Search Report issued by the International Searching Authority (ISA/O.E.P.M.) dated Sep. 24, 2018 in connection with International Application No. PCT/ES2018/070289.
Dec. 17, 2020 Supplementary European Search Report issued by the European Patent Office in connection with International Application No. EP 18 77 6647.
European Patent Application Publication EP 1 656 939 A1 (Kruisinga), published on May 17, 2006.
European Patent Application Publication EP 2 702 988 A2 (Chen Chien-Hung [US])), published on Mar. 5, 2014.
Melancon, K. et al, "Regression of NMU-induced mammary tumors with the combination of melatonin and 9-cis-retinoic acid", Cancer Letters, 2005, vol. 227, pp. 39-48.

* cited by examiner

*Primary Examiner* — Golam M Shameem
(74) *Attorney, Agent, or Firm* — Gary J. Gershik; Amster Rothstein & Ebenstein LLP

(57) ABSTRACT

The present invention relates to the use of melatonin for the preparation of a pharmaceutical composition suitable for intratumoral administration for the treatment of tumors. This composition comprises high concentrations of melatonin, melatonin derivatives or metabolites, such that melatonin exerts an oxidizing effect, increasing the production of free radicals and activating cell death.

14 Claims, 5 Drawing Sheets

USE OF MELATONIN FOR THE TREATMENT OF TUMORS

CROSS-REFERENCE TO RELATED APPLICATIONS

This application is a § 371 national stage of PCI International Application No. PCT/ES2018/070289, filed Apr. 2, 2018, claiming priority of Spanish Patent Application No. P201730598, filed Mar. 31, 2017, the contents of each of which are hereby incorporated by reference into this application.

FIELD OF THE ART

The present invention is comprised generally in the medical and pharmaceutical field. In particular, the present invention describes the use of melatonin for the treatment of tumors by means of intratumoral administration.

STATE OF THE ART

Current Cancer Treatment

Drug resistance is one of the main limitations in clinical oncology and the cause of relapse in many patients, so the search for new therapeutic targets, as well as the search for drugs enhancing the cytotoxic effects of standard treatments, without enhancing the adverse effects, becomes fundamental.

Current cancer treatment is based on the application of surgery, chemotherapy, and/or radiotherapy, alone or together. The primary treatments are radiotherapy, surgery, or a combination of both, where chemotherapy is often used as additional or adjuvant treatment. For example, head and neck cancer, referred to as head and neck squamous cell carcinoma (HNSCC), is one of the six most common cancers and represents an incidence of approximately 650000 new diagnosed cases and a mortality of about 350000 persons a year worldwide. Cancers that are known collectively as head and neck cancers usually begin in the squamous cells that line the moist, mucosal surfaces inside the head and neck (National Cancer Institute, Head and Neck Cancers). In Spain, the incidence of head and neck cancer for the year 2015 was estimated at 16.298%, It is estimated that head and neck cancer affects 14.483% of men and 1.815% of women, whereas its incidence in women is estimated to increase in the year 2017.

The three main types of treatments for managing head and neck cancer are radiotherapy, surgery, and chemotherapy. The primary treatments are radiotherapy, surgery, or a combination of both, where chemotherapy is often used as additional or adjuvant treatment. Cisplatin is used, and in more resistant cases cetuximab. The optimal combination of the three forms of treatment for a patient with head and neck cancer depends on the site and stage of the disease. There are some new treatments, as well as new combinations of old treatments. A good example of the latter is the use in recent years of a combination of radiotherapy and chemotherapy or immunotherapy for the treatment of advanced head and neck cancer. However, these treatments exhibit a high degree of toxicity in healthy cells. Chemotherapy and radiotherapy treatment is associated with short- and long-term side effects. Mucositis, epithelitis, malnutrition, tracheitis and arytenoid edema, xerostomia, ageusia, nephrotoxicity, vomiting, and myelosuppression are the most significant acute effects of treatment in patients with head and neck tumors. The onset of a series of late effects, such as xerostomia, hypogeusia, hypothyroidism, tooth alteration, trismus, bone or cartilage necrosis, cervical myelitis, hypoacusia, cataracts, and retinopathy, can also be observed. Mucositis is the most common and important of all the acute effects of cancer treatment, constituting the main cause of treatment interruption.

Although the prognosis depends on multiples factors, it can be said in general that the 1-year survival rate is 75% and the 5-year survival rate is 42%. The general characteristics of head and neck cancers include, among others, the absence of early diagnosis, where many of them show up in advanced phases and with symptoms similar to common diseases which may delay definitive diagnosis, the absence of effective screening, the tendency for local relapse rather than distant metastasis, and the ability to affect one or more important, and even vital, functions such as swallowing, respiration, and speech. Unfortunately, up to 75% of patients with head and neck cancer are diagnosed with a locally advanced disease. In these more advanced stages, more recent strategies such as induction chemotherapy and/or chemoradiotherapy have been integrated in the local treatment; however, the 5-year survival rate remains about 30%, and 60% of the patients will experience a local-regional or distant relapse 2 years following the initial treatment. Extremely unfavorable situations may also occur where patients with head and neck cancer suffer a recurrence or experience metastasis. The standard treatment for recurred or metastatic head and neck cancer is chemotherapy with platinum or cetuximab, generally with doublets, obtaining a higher response rate of about 30% with respect to monotherapy, but not a higher 6 to 8-month survival rate. An even more disheartening situation would arise following the failure of this treatment. Accordingly, there is a desperate need for new treatments that are more effective and can provide a better safety profile in head and neck cancer. This is the reason for the development of new drugs or combinations of drugs in the advanced refractory disease.

In summary; tumor resistance is the problem faced in anti-tumor therapy today. For this reason, therapeutic agents with an acceptable toxicity profile must be provided.

Melatonin

Melatonin (N-acetyl-5-methoxytryptamine) is an endogenous hormone synthesized from tryptophan and produced by the pineal gland. At present, it is known that melatonin is also produced in various tissues and organs at much higher concentrations than that produced in the pineal gland [Acuña-Castroviejo et al. Cell Mol Life Sci 2014, 71, 2997-3025].

Melatonin is a powerful antioxidant which, in addition to scavenging free radicals, increases the expression and activity of endogenous antioxidant enzymes such as superoxide dismutase (SOD), catalase, glutathione peroxidase (GPx), glutathione reductase (GRd), and γ-glutamyl-cysteine synthetase. Furthermore, as it eliminates free radicals, melatonin generates a series of metabolites which are also free radical scavengers that are as powerful as melatonin itself (Urata, Y et al. Free Radio Biol Med 1999, 27, 838-847). In other words, melatonin is more effective than other antioxidants in preventing damage caused by oxidative stress.

Furthermore, due to its physicochemical properties, melatonin goes through all the membranes, reaching all cellular compartments, including the mitochondrion where it is capable of maintaining mitochondrial homeostasis in different experimental models (Acuna-Castroviejo et al. Cell Mol Life Sci 2014, 71, 2997-3025; Diaz-Casado et al. J Pineal Res 2016, 61, 96-107; Doerrier et al. Mitochondrion 2016, 27, 56-63). Melatonin increases membrane fluidity, electron transport chain (ETC) complex activity, ATP production, and mitochondrial membrane potential, while reduces oxidative stress and mitochondrial permeability transition pore closure.

Moreover, melatonin has significant anti-inflammatory effects including the inhibition of the expression of iNOS/i-mtNOS, COX-2, and pro-inflammatory cytokines such as IL-1β or TNF-α. Many of these properties are attributed to the inhibition of the NF-κ B pathway depending on the function of the innate immunity pathway (Escames et al, FASEB J 2003, 17, 932-934; Escames et al. Journal of Pineal Research 2006, 40, 71-78).

It has also been demonstrated recently that melatonin inhibits the NLRP3 inflammasome pathway in different experimental conditions (Ortiz et al. J Pineal Res 2015, 58, 34-49; Garcia et al, FASEB J 2015, 29, 3863-3875; Volt et al. J Pineal Res 2016, 60, 193-205). It has also been demonstrated that a melatonin gel prevents the onset of mucositis in irradiated rats, inflammation, and duodenal necrosis, and restores mucosal endogenous melatonin levels of the irradiated animals (Ortiz et al, J Pineal Res 2015, 58, 34-49), A clinical trial is currently being carried out with this gel in patients with head and neck cancer to prevent oral mucositis.

Melatonin has been administered to patients admitted to intensive care units (Mohan and Brunner, 2005. Acta Anaesthesiol Scand 49:1397). Its intravenous use in newborns with sepsis leads to a significant decrease in mortality without any side effects (Gitto et al., 2004. J PediatrSurg 39: 184).

The usefulness of intravenous administration in patients with sepsis using an injectable melatonin composition has also been demonstrated [WO 2015/144965].

Cancer Treatment by Means of Melatonin

Various papers have demonstrated that melatonin contains significant oncostatic properties. Its antiproliferative properties have been demonstrated in a wide variety of tumors, including breast, endometrial, prostate, colon, and ovarian cancers, as well as choriocarcinoma, melanoma, neuroblastoma, and osteosarcoma, among others (Lissoni et al. Anticancer Res 2000, 20, 2103-2105; Hong et al. J Pineal Res 2014, 56, 264-274). Melatonin directly inhibits tumor cell proliferation and growth (Ma et al, Oncotarget 2016, 7, 46768-46784). Melatonin protects normal cells from apoptosis while at the same time increases apoptotic cell death in several types of cancerous cells (Trubiani et al. J Pineal Res 2005, 39, 425-431). Its immunomodulating anticarcinogenic action also increases anti-tumor immune response (Miller et al. Int J Exp Pathol 2006, 87, 81-87). Furthermore, melatonin has a significant metabolic effect as it reduces glucose intake by cancerous cells, and accordingly inhibits tumor growth through the suppression of linoleic acid absorption and the metabolism thereof by the tumor to produce the mitogenic molecule 13-NODE (Blask et al. Cancer Res 1999, 59, 4693-4701). The anti-angiogenic and anti-metastatic properties of melatonin have also been demonstrated in various studies (Tischer et al. J Biol Chem 1991, 266, 11947-11954; Park et al. J Pineal Res 2010, 48, 178-184.; Su et at, J Pineal Res 2017, 62). Given the capacity of this molecule to increase anti-tumor drug efficacy, this data shows that melatonin can be used not only for treating mucositis due to the absence of adverse side effects, but can also be used in cancer co-treatment programs.

Despite the plethora of papers demonstrating the oncostatic effects of melatonin in tumor cells, there is no study in which melatonin is seen to destroy tumor. Up until now, it has been seen in mice that melatonin can reduce the size of tumor without the tumor disappearing completely. In other words, there is a certain degree of melatonin resistance in animals.

Drug resistance is one of the main limitations in clinical oncology and the cause of relapse in many patients, so the search for new therapeutic targets, as well as the search for drugs enhancing the cytotoxic effects of standard treatments, without enhancing the adverse effects, becomes fundamental.

There are many examples of drugs which exhibit a cytotoxic behavior in tumor cells in vitro but lose their efficacy in vivo or in clinical setting. In many cases, this chemoresistance is due to microenvironment of the tumor.

Intralesional injection techniques Various cancer treatments by means of intralesional injection techniques, by means of the intratumoral injection of ethanol, acetic acid, hot serum, or chemotherapeutic agents, are also described in the state of the art.

In particular, the intratumoral injection of ethanol is a simple and cost-effective technique used in the treatment of hepatocarcinomas, particularly encapsulated hepatocarcinomas.

Intratumoral Compositions Comprising Melatonin

[U.S. Pat. No. 9,289,428 B2] describes the intratumoral administration of antioxidants as ocular cancer therapy by means of reducing the formation of free radicals in the tumor. However, although the formulation contemplates the possibility of using melatonin, it describes a dose of 19 pg/ml of melatonin to exert such antioxidant effects. At these concentrations, melatonin produces an effect which does not increase mitochondrial function, so free radicals which can activate cell death are not produced.

Therefore, although it is known that melatonin inhibits cell proliferation and increases cell death provided that suitable amounts of same enter the tumor cell, the use of melatonin such that it allows reducing recurrences in cancer treatment, as well as resistance to oncostatic treatments, has not been described up until now.

BRIEF DESCRIPTION OF THE INVENTION

The present invention relates to a pharmaceutical composition for intratumoral administration comprising high concentrations of melatonin, melatonin derivatives, or metabolites, such that the melatonin exerts an oxidizing effect, in contrast to the regular use thereof, and particularly to the use thereof proposed, for example, in [U.S. Pat. No. 9,289,428 B2]. It increases mitochondrial function, and accordingly the production of free radicals activating cell death.

In a second aspect, the present invention relates to the use of melatonin, particularly the use of the mentioned intratumoral composition, for the treatment of tumors, preferably for the elimination of tumors.

The invention also describes a method of treatment comprising the intratumoral administration of a therapeutically effective amount of melatonin.

DETAILED DESCRIPTION OF THE INVENTION

Definitions

Figure 1:
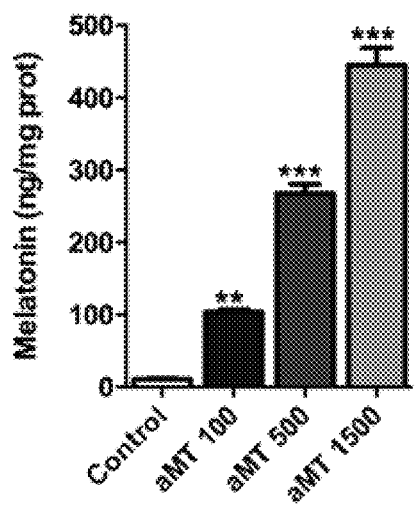
FIG. 1. Analysis of melatonin penetration in tumor cells. It is observed that melatonin readily enters the tumor cells in a dose-dependent manner in the in-vitro experiments. It reaches maximum levels of 450 ng/mg of proteins after incubating the cells with melatonin at a dose of 1500 μM for 24 hours.

The term "intratumoral administration" used herein includes any technique which allows introducing a compound of general formula X, particularly melatonin, into a tumor. These techniques include, among others, injection, electroporation or electropermeabilization, ultrasound-mediated administration, creams, lotions, or other dosage forms.

The term "treatment" or "treat" in the context of this document refers to the administration of a compound or a composition according to the invention for improving or eliminating a disease, pathological condition, or one or more symptoms associated with said disease or condition in a mammal, preferably in humans. "Treatment" also covers improving or eliminating the physiological consequences of the disease. Specifically, the concept "treat" can be interpreted as:
i. Inhibiting the disease or pathological condition, i.e., stopping its development;
ii. Alleviating the disease or pathological condition, i.e., causing the regression of the disease or pathological condition;
iii. Stabilizing the disease or pathological condition.

Particularly, the term treatment includes the selective destruction of tumor cells, and particularly the complete elimination of a tumor.

Throughout the description and the claims, the term "comprises" can also be interpreted as "consists of" and the variants thereof do not intend to exclude other technical features, additions, components, or steps. For those skilled in the art, other objects, advantages, and features of the invention will be inferred in part from the description and in part from the practice of the invention.

Pharmaceutical Compositions

In a second aspect, the invention provides pharmaceutical compositions, formulations, or dosage forms for the treatment of tumors by means of intratumoral administration, hereinafter "compositions of the invention," comprising a therapeutically effective amount of at least one melatonin-derived compound as an active ingredient.

In a particular embodiment, the compositions of the invention are suitable for the treatment of malignant tumors, preferably tumors associated with head and neck cancer, melanoma, breast tumors or breast cancer-associated tumors, ocular tumors, urologic tumors, such as testicular tumors, and hepatic tumors, such as hepatocarcinoma, cervical tumors, lymphomas, thyroid tumors, soft part sarcoma.

Melatonin derivative is defined according to formula X and includes salts, prodrugs, or solvates thereof:

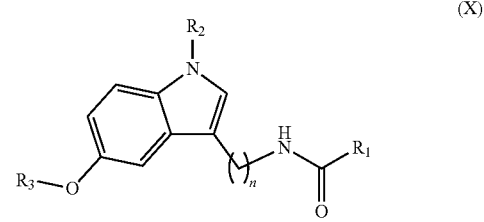

where:
n is an integer between 1 and 4; preferably of 1, 2, or 3.
R1 and R3 are independently selected from the group consisting of linear or branched $C_1$-$C_4$ alkyl;
R2 is hydrogen, linear or branched ($C_1$-$C_4$)alkyl, a —C(=O)O—Ra group or a —C(=O)—N(H)—Ra group, wherein Ra is a linear or branched ($C_1$-$C_4$)alkyl group;

The term "alkyl" refers herein to linear or branched aliphatic chains having 1 to 4 carbon atoms, for example, methyl, ethyl, n-propyl, i-propyl, n-butyl, tert-butyl, sec-butyl, n-pentyl, etc. Preferably, the alkyl group has between 1 and 2 carbon atoms, and it is more preferably a methyl group.

In a preferred embodiment, the active ingredient of the composition of the invention is melatonin (N-acetyl-5-methoxytryptamine), a salt, prodrug, or solvate thereof.

The term "melatonin" refers to N-acetyl-5-methoxytryptamine, also referred to in the literature as melatonin, melatonine, melatol, melovine, circadin, regulin, acetaminde, N-acetyl-methoxy-tryptamine, 5-methoxy-N-acetyltryptamine, N-[2-(5-methoxy-1H-indol-3-yl)ethyl]acetamide, or N-[2-(5-15-methoxyindol-3-yl)ethyl]acetamide, or when in the compound of general formula (I) R1 and R3 are a methyl group, n is 1 and R2 is hydrogen.

The CAS number of melatonin is 73-31-4.

Therefore, the present invention also relates to the pharmaceutically acceptable salts of melatonin or melatonin derivatives which can be generated by means of chemical methods known by one skilled in the art, for example, by means of a reaction with an acid in water or in an organic solvent or in a mixture of the two. Ether, ethyl acetate, ethanol, isopropanol, or acetonitrile can be used as organic solvent. The examples of acid addition salts include mineral acid addition salts, such as hydrochloride, hydrobromide, hydroiodide, sulfate, nitrate, phosphate, for example, and organic acid addition salts such as acetate, maleate, fumarate, citrate, oxalate, succinate, tartrate, malate, mandelate, methanesulfonate, and p-toluenesulfonate, for example.

The term "prodrug," as it is used herein, refers to a chemical compound which has undergone a chemical derivation, for example, a substitution or addition of an additional chemical group to modify any of its physicochemical properties, such as solubility or bioavailability, but not the technical characteristics of the original molecule. A prodrug would be, for example, an ester, ether, or amide derivative. Bioavailability refers to the availability of the prodrug in a specific biological compartment.

The term "solvate" according to this invention must be understood to be that melatonin derivative having another molecule, for example, a polar solvent, bound by means of a non-covalent bond. Examples of such solvates include hydrates and alcoholates, for example, methanolates.

The salts, solvates, and prodrugs can be prepared by means of methods known in the state of the art. Non-pharmaceutically acceptable salts, solvates, or prodrugs also fall within the scope of the invention because they may be useful in the preparation of pharmaceutically acceptable salts, solvates, or prodrugs. The composition of the invention can also refer to a composition comprising a functional biological equivalent of melatonin in a concentration which is equivalent to that described in the compositions of the invention.

The term "functional biological equivalent" or "bioequivalent variable," as it is used herein, refers to a molecule with the same function as the described molecule, this molecule being able to exhibit slight variations with respect to the described molecule without said variations leading to said molecule having any additional technical effect. In the present invention, it therefore refers to melatonin variants having the same function and exhibiting slight variations without said variations leading to the melatonin having any additional technical effect.

"Concentration which is equivalent" is understood to be that concentration required for the functional biological equivalent of melatonin to produce the same effect as the effect described in the present invention for the composition of the invention.

Melatonin is also produced in plants. For example, the presence of melatonin has been described in algae, edible plants, cereals, fruits, seeds, roots, stems, leaves, and medicinal herbs. For example, the presence of melatonin has been described in cocoa, grapes, tomatoes, tea, green tea, algae, cereals, and olives. Therefore, the melatonin of the composition of the invention can be of plant origin. Melatonin of plant origin (also referred to as phytomelatonin) can be obtained by means of any method known by one skilled in the art for such purpose.

The melatonin used in the composition of the invention can also be of synthetic origin. The chemical synthesis of melatonin can be performed by means of techniques known by one skilled in the art for such purpose.

In a particular embodiment, the composition of the invention is suitable for administration by intratumoral injection.

Dosage for the purpose of obtaining a therapeutically effective amount depends on a variety of factors, such as the type of tumor, preferably mammal tumor, and more preferably human tumor.

In the sense used in this description, the expression "therapeutically effective amount" refers to that amount of a compound of the invention which, when administered to a mammal, preferably humans, is sufficient to cause the treatment of a disease or pathological condition of interest in the mammal, preferably humans. The amount of compound X, metabolite, salt, solvate, or prodrug constituting a therapeutically effective amount will vary, for example, according to the activity of the specific compound used; the metabolic stability and the duration of action of the compound; the species (preferably human), the type of tumor, the age, body weight, general condition of health, sex, and diet of the patient, the route of administration, the mode and time of administration, the excretion speed, the combination of drugs, the severity of the particular disorder or pathological condition, and the subject who is subjected to therapy, but it can be determined by one skilled in the art according to their knowledge and that description.

In a particular embodiment, the concentration which gives rise to the therapeutically effective amount of the compound of formula X, preferably melatonin, is greater than 0.1% (w/v) with respect to the total composition being administered. Preferably, this concentration is greater than 0.2% (w/v), more preferably greater than 0.3% (w/v), even more preferably it is comprised between 0.3 and 5% (w/v), and even more preferably between 0.3 and 4.5% (w/v).

In a particular embodiment in which administration is performed by means of intratumoral injection, the concentration of the compound of formula X, preferably melatonin, which gives rise to the therapeutically effective amount is greater than 0.1% (w/v) with respect to the total composition being administered, preferably greater than 0.2% (w/v), more preferably it is comprised between 0.2% and 0.5%, and still more preferably it is 0.3% (w/v).

Therefore, in comparison with the concentration described in the state of the art the composition of the invention comprises melatonin with a concentration of at least 0.16 million times greater.

Said formulations can contain any other active ingredient in the treatment of tumors or can be characterized by containing, as an active ingredient, only a compound of general formula X or a combination of compounds of general formula X.

Another preferred embodiment relates to the use in which the composition further comprises at least another active ingredient. As it is used herein, the terms "active principle," "active substance," "pharmaceutically active substance," "active ingredient" or "pharmaceutically active ingredient" refers to any component which potentially provides a pharmacological activity or another different effect in the diagnosis, cure, mitigation, treatment, or prevention of a disease, or which affects the structure or function of the body of human beings or other animals. For example, other oncostatic molecules can be used.

In addition to the therapeutic efficacy requirement which may require the use of therapeutic agents, in addition to the compounds of the invention, there may be additional fundamental reasons which greatly compel or suggest the use of a combination of a compound of the invention and another therapeutic agent, such as in the treatment of diseases or conditions directly or indirectly modulating the function of the substance.

According to the present invention, "dosage form" is the individual arrangement to which drugs (active ingredients) and excipients (pharmacologically inactive matter) are adapted to constitute a medicinal product.

The formulations can furthermore contain pharmaceutically acceptable excipients or adjuvants.

The excipients and vehicles used must be pharmaceutically and pharmacologically tolerable, such that they can be combined with other components of the formulation or preparation and do not exert adverse effects in the treated organism.

The term "excipient" refers to a substance which helps in the absorption of the pharmaceutical composition or medicinal product of the invention, stabilizes said pharmaceutical composition, or helps in its preparation in the sense of providing consistency thereto. Therefore, the excipients may perform the function of keeping the ingredients together, such as starches, sugars, or celluloses, of protecting the medicinal product, for example to isolate the same from air and/or moisture.

A "pharmaceutically acceptable vehicle" or a pharmacologically acceptable vehicle refers to those substances or combination of substances known in the pharmaceutical sector, used in the elaboration of pharmaceutical dosage forms, and includes, but without limitation, solids, liquids, solvents, or surfactants. The vehicle can be a an inert substance or a substance with an action similar to any of the compounds of the present invention. The function of the vehicle is to facilitate the incorporation of the expression product of the invention as well as other compounds, allow improved dosing and administration, or provide consistency and shape to the pharmaceutical composition. When the form of presentation is liquid, the vehicle is the diluent. The pharmaceutically acceptable vehicles which can be used in the invention can be those known by one skilled in the art, for example, lysosomes, millicapsules, microcapsules, nanocapsules, sponges, millispheres, microspheres, nanospheres, milliparticles, microparticles, and nanoparticles.

The best dosage form will depend on the type of tumor and on the condition of the patient.

In the case of injectable administration, an example of pharmaceutically acceptable vehicle is 10% propylene glycol (PG) and isotonic saline solution.

The pharmaceutical compositions or formulations must be suitable for intratumoral administration by means of injection, electroporation or electropermeabilization, ultrasound-mediated administration, creams, lotions, or other dosage forms.

The term "adjuvant" refers to any substance which enhances the response of an active ingredient. In the present invention, it refers to any substance which enhances the effects of the composition of the invention, and it can refer to any adjuvant known by one skilled in the art.

The term "pharmaceutically acceptable" refers to the fact that the compound to which reference is made is allowed and evaluated such that it does not cause any damage to the organisms to which it is administered.

Another preferred embodiment relates to the use in which the composition further comprises a gelling agent. Preferably, the gelling agent is selected from the list comprising polyethylene and polypropylene copolymer, cellulose, and guar gum. Preferably, it relates to polyethylene and polypropylene copolymer. As described herein, another preferred embodiment relates to the use in which the composition is a gel (or also referred to as "hydrogel").

In the case of intratumoral administration, particularly injectable administration of a gel, an example of pharmaceutically acceptable vehicle is a 5% isotonic pluronic solution.

The term "gelling agent" refers to a substance forming a gel, i.e., a three-dimensional network formed by the gelling agent and generally containing a liquid phase.

Therefore, the gelling agents which can be used for manufacturing the gel which is administered intratumorally can be those known by one skilled in the art for the elaboration of a pharmaceutical composition. For example, among polyethylene and polypropylene copolymers, poloxamer copolymers (or poloxamer), for example the agents referred to as Pluronic® including, among others, Pluronic® F127 (CAS number 9003-11-6) or Pluronic® F127NF, can be used.

In another preferred embodiment, the composition further comprises at least one preservative.

"Preservative" is understood to be that substance which maintains the properties of the medicinal product by inhibiting contamination by germs, and they can be ionic or non-ionic preservatives. The preservative used must not be toxic, must be chemically stable and compatible with melatonin. Those preservatives known in the state of the art can be used as preservative agents, for example, the preservative can refer to benzoic acid, sodium benzoate, ascorbic acid, potassium sorbate, methylparaben, ethylparaben, or butylparaben. "Germs" is understood to be any cell that can grow and multiply in the composition of the invention, for example bacteria, fungi, and yeasts.

The amounts of active substances to be administered can vary depending on the particularities of the therapy.

The compositions of the invention are prepared using standard methods such as those described or referred to in the Spanish and United States Pharmacopoeias and similar reference texts.

Combined Preparations

The term "combined preparation" or also referred to as "juxtaposition" herein means that the components of the combined preparation need not present as a union, for example in a true composition, to be available for combined, separate, or sequential application. Therefore, the expression "juxtaposed" means that it is not necessarily a true combination in view of the physical separation of the components.

Therefore, in another aspect the invention relates to a composition, preparation, or dosage form suitable for intratumoral administration, hereinafter "combined preparation of the invention," comprising:

a) a therapeutically effective amount of the compound of general formula X, preferably melatonin, and b) another active ingredient against tumors.

Kit of the Invention

In another aspect, the present invention relates to a kit ("kit of parts") for the preparation of the composition or the combined preparation of the invention.

As it is used herein, the term "kit" refers to a combination of a set of components which are suitable for obtaining the composition or the combined preparation of the invention, may or may not be packaged together, along with their containers and packaging suitable for marketing, etc.

In the present invention, "component suitable for obtaining the composition or the combined preparation of the invention" is understood to be any compound which can be used for obtaining same and includes, without limitation, aqueous solutions, solid preparations, buffers, syrups, preservation solutions, flavoring agents, pH correctors, thickeners, etc.

The components of the kit can be provided in separate vials (in the form of "kit of parts") or in a single vial. Furthermore, the kit of the present invention is understood to as being intended for the preparation of the composition or the combined preparation or the dosage form of the invention. Preferably, the components of the kit of the present invention are ready-to-use components for preparing the composition or the combined preparation or the dosage form of the present invention. Furthermore, the kit preferably contains instructions explaining how to prepare the composition or the combined preparation or the dosage form of the present invention. The instructions can be provided to users in electronic or printed format.

Therefore, the invention provides a kit for the preparation of the composition of the invention or the combined preparation of the invention, a container comprising a receptacle with the compound of general formula X in any pharmaceutically acceptable formulation, together with components suitable for obtaining the composition or the combined preparation of the invention.

Particularly, the kit of the invention further comprises a receptacle with the compound of general formula X in any pharmaceutically acceptable formulation.

Use of the Compounds of the Invention

A third aspect of the invention consists of the use of a compound of general formula X, a salt, a solvate, or a prodrug thereof for the preparation of a pharmaceutical composition for the treatment of a tumor, in which the pharmaceutical composition is administered intratumorally.

Accordingly, the invention relates to the use of the compositions and/or the combined preparations, and/or the kit of the invention as a medicinal product or for the elaboration of a medicinal product suitable for the treatment of tumors, preferably solid tumors, more preferably malignant tumors.

A tumor is considered malignant when the cells forming same have the capacity to spread to other areas of the body and can also grow in these organs, causing metastasis.

In another aspect, the present invention relates to a method for the treatment of patients affected by a tumor, hereinafter "method of treatment of the invention" by means of using the compounds and/or the compositions and/or the combined preparations and/or the kit of the invention. The effects of this method of treatment include, but are not limited to, tumor elimination, increase in disease progression time, and survival index. The effects of treatment include a longer-term disease control.

In a preferred embodiment, the treatment consists of the complete elimination of the tumor.

This treatment consists of administering, to the individuals affected by these diseases, therapeutically effective amounts of a compound of the invention or a pharmaceutical composition including same.

The administered amount depends on tumor size and localization.

Preferably, between 30 and 100 µl, preferably between 40 and 80 µl, more preferably 60 µl of the composition of the invention is administered per 100 mm$^3$ of tumor.

In a preferred embodiment, the tumor which is treated using the compositions and/or the combined preparations and/or the kit of the invention and/or the method of treatment of the invention is a malignant tumor selected from the group consisting of carcinogenic tumors, preferably tumors associated with head and neck cancer, melanoma, breast tumors or breast cancer-associated tumors, ocular tumors, urologic tumors, such as testicular tumors, and hepatic tumors such as hepatocarcinoma, cervical tumors, lymphomas, thyroid tumors, and soft part sarcoma.

The compositions of the invention alone or in combination with other compounds, compositions, or medicinal products, can be administered by means of the modes of administration of accepted agents to serve similar usefulness.

EMBODIMENTS

The following examples are provided by way of illustration and do not seek to limit the present invention:

Methodology

First, it was demonstrated that melatonin increases the levels of free radicals in the cell. The relationship between the mitochondrial changes caused by melatonin and the cell death induced by this molecule in these tumor cells was studied. Melatonin increases the number of mitochondria as well as the number of cristae, DNA, and mitochondrial mass. The result is an increase in respiratory chain complexes, and accordingly an increase in oxygen consumption, which is related to an increase in free radicals and oxidative stress reflected by an increase in the GSSG/GSH ratio. However, the antioxidant capacity is not modified. The activity and the expression of antioxidant enzymes such as GPx and the GRd is not modified either. A slight increase in SOD is observed. Moreover, SCC-9 cells, that are more resistant to melatonin, exhibit less mitochondrial changes with melatonin, and accordingly less production of reactive oxygen species (ROS).

Moreover, it has been demonstrated that although the number of mitochondria increases, these are not functional mitochondria as ATP production does not increase. However, the metabolomics studies demonstrate an increase in all the intermediate products of the Krebs cycle. In other words, mitochondrial activity increases, and accordingly free radicals which induce cell death also increase.

To carry out the assays, CAL-27 and SCC9 cells have been used as typical example of head and neck squamous cell carcinoma (HNSCC) cancer cells.

For the in vivo assays, athymic nude mice (nu/nu) (Janvier, Pays de la Loire, France) of about 5-6 weeks of age (18-20 g) were used. The animals were held in the animal housing unit of the Biomedical Research Center of University of Granada (CIBM) in sterile conditions and under controlled photoperiod (12:12 h) and temperature (22±1° C.) environments, with ad libitum water and laboratory diet. The handling and transplant of the animals was carried out in a laminar flow biosafety cabinet. The animals were anesthetized with an i.p. injection of ketamine (80 mg/kg) and xylazine (4 mg/kg).

Xenografts were performed with CAL-27 and SCC9 cells (the latter being resistant to melatonin). Cells enzymatically separated with trypsin-EDTA are resuspended at a concentration of $4\times10^6$ cells per mouse in PBS. Cell viability is determined by means of the Trypan Blue test. The cells are injected into the left flank of the mouse, with a volume of 200 µL of cell suspension being injected into each mouse with the help of a 1 mL syringe with a needle measuring 16×0.5 mm.

The body weight and tumor size are measured and recorded two or three times a week throughout the experiment. The tumor volume is calculated using the following formula: ½ (L×W2) (mm$^3$), where L is the length and W is the width. After the appearance of a tumoral node (100 mm³), the mice carrying the tumors are randomly assigned to several groups.

The experimental groups were as follows:
1. Mouse with untreated tumor
2. Mouse with tumor treated with subcutaneously administered melatonin (s.c.) at a dose of 300 mg/kg (4.5% w/v melatonin solution). The concentration of melatonin in the tumor when melatonin is administered through this route is 10 ng/mg of proteins.
3. Mouse with tumor treated with administered intratumorally melatonin (60 µl of a 0.1% w/v melatonin solution) fora tumor volume of 100 mm³. 0.1% of melatonin is the minimum effective dose (in vitro) for inducing 80% cell death. When 0.1% of melatonin is administered, a concentration of 450 ng/mg of proteins is reached in the tumor.
4. Mouse with tumor treated with intratumorally melatonin administered (60 µl of a 4.5% melatonin solution) for a tumor volume of 100 mm³.

4.5% melatonin is the maximum dose used s.c. in vivo.

Therefore, once the tumor reached the indicated volume of 100 mm³, it is treated with melatonin daily for 21 days according to the following protocol:
A. Injected s.c. (300 mg/kg which is equivalent to a 4.5% solution)
B. Injected directly into the tumor (60 µl of a 0.1% melatonin solution)
C. Injected directly into the tumor (60 µl of a 4.5% melatonin solution)
D. Injected directly into the tumor (60 µl of a 0.1% melatonin solution) until the complete disappearance of the tumor (28 days).
E. Photographs of the tumor were taken at the end of the treatment of each of the groups. Likewise, an NMR analysis was performed upon the completion of treatment to see tumor activity.

Results:

In Vitro Result Analysis

In the in-vitro experiments, the tumor cells were incubated with different concentrations of melatonin. It was observed that melatonin readily enters the tumor cells, reaching levels of 450 ng/mg of proteins after incubating the cells with melatonin at a dose of 1500 µM for 24 hours (FIG. 1).

It has been demonstrated that, at high concentrations, melatonin activates the apoptotic mechanisms in tumor cells by acting on the mitochondria of said cells, in addition to enhancing the cytotoxic effects of radiotherapy and chemotherapy. A significant decrease has been observed in the size and number of colonies of tumor cells (CAL-27) irradiated and treated with melatonin. Melatonin increases apoptosis in a dose and time dependent manner. Inhibition of cell proliferation and stopping of cell cycle in the S and G2 phases have also been observed. The relationship between the mitochondrial changes caused by melatonin and the cell death induced by this molecule in these tumor cells has been studied. Melatonin increases mitochondrial mass, mitochondrial DNA, the number of mitochondria, as well as the number of mitochondrial cristae. The result is an increase in respiratory chain complexes, and accordingly an increase in oxygen consumption, which is related to an increase in free radicals and oxidative stress. Furthermore, it is observed that melatonin does not increase the activity of antioxidant enzymes such as GPx or GRd, which leads to an even greater production of free radicals. In other words, the cytotoxic effects of melatonin in the tumor cells are related to an increase in mitochondrial function, and the increase in mitochondrial function in the tumor cell in turn induces apoptosis processes, which also entails the inhibition of protein synthesis. Moreover, it has been confirmed that SCC-9 head and neck cancer cells are more resistant to melatonin, with less effect on mitochondrial function, and therefore a lower production of free radicals, being observed at the same time. These results indicate that melatonin enters these cells at lower concentration.

In Vivo Result Analysis

A dose-response study with melatonin was performed in mice xenografted with Cal-27 cells and it was observed that the maximum amount of melatonin entering the tumor after 21 days of treatment is only 14 ng/mg of proteins despite the use of doses of up to 300 mg/kg. However, in the in vitro experiments, the levels of melatonin reach 450 ng/mg of proteins 24 hours after treatment with 1500 µM of melatonin. Therefore, there is a mechanism which hinders the entry of melatonin in the tumor cell in the tumor in vivo as well as in specific types of tumor cells.

Figure 2:
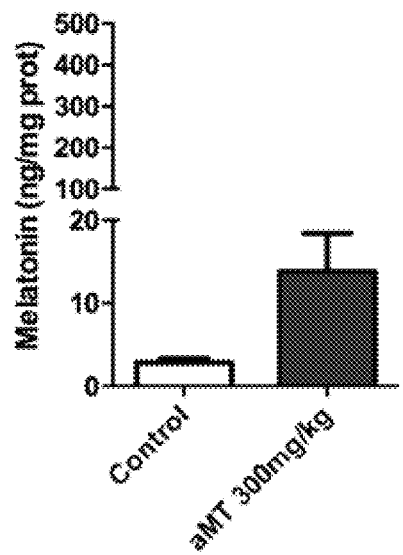
FIG. 2. Analysis of the penetration of subcutaneously administered melatonin in the tumor. It is observed that melatonin enters the tumor in very small amounts (10 ng/mg of proteins) when it is administered subcutaneously, despite the fact that it is administered at very high doses (300 mg/kg) for a prolonged time (21 days).

In the in-vivo experiments, melatonin was administered subcutaneously at a dose of 300 mg/kg. However, it has been observed that the amount of melatonin entering the tumor is negligible (14 ng/mg of proteins) despite the administration of a melatonin dose of 300 mg/kg of weight of the mouse (FIG. 2), which indicates that there is a certain mechanism which prevents the entry of sufficient amounts of melatonin to exert its effects in the tumor cell.

The concentration of melatonin in the tumors was measured after sacrificing the animals after 21 days. When it is injected directly into the tumor, the concentration of melatonin cannot be measured due to the limited amount of sample taking into account that the tumor practically disappears.

Figure 3:
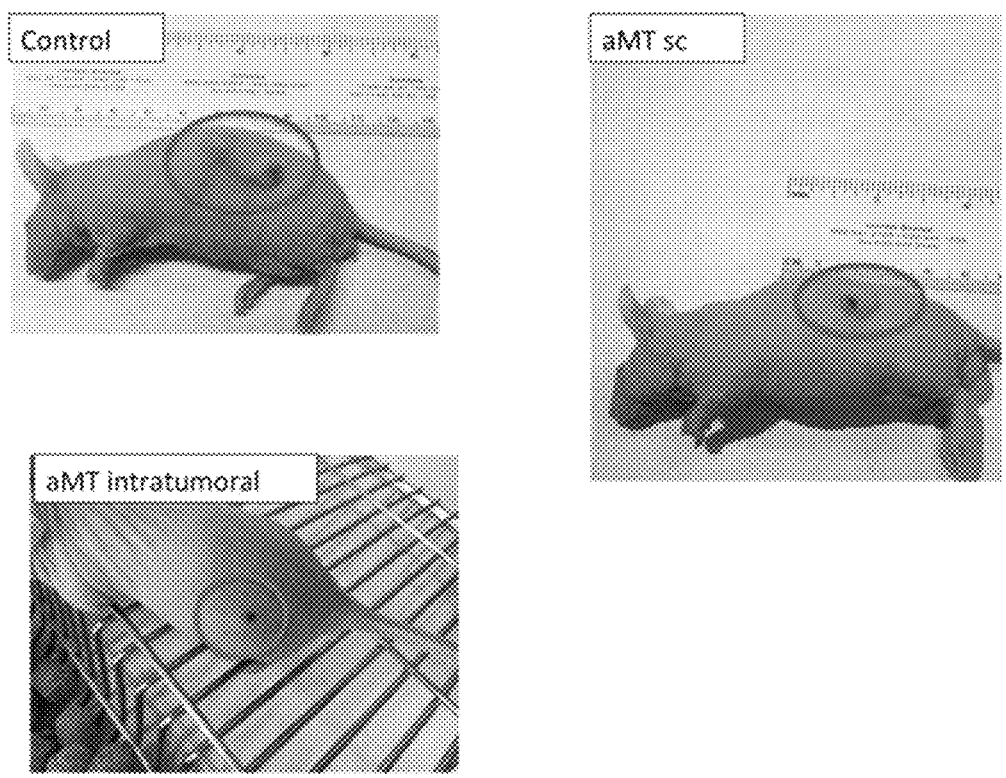
FIG. 3. Analysis of the tumor volume by comparing intratumoral melatonin administration with the control. However, when melatonin reaches the tumor through the systemic route, the decrease in tumor volume is much lower despite the administration of high doses.

Moreover, when melatonin is administered subcutaneously at a dose of 300 mg/kg, the tumor volume decreases very little with respect to the control (FIG. 3). Neither increasing the dose of melatonin above 300 mg/kg of weight, nor increasing the days of treatment, allows observing an increase in the effect of melatonin on the tumor. In other words, melatonin does not enter the tumor in a higher amount. However, the tumor volume decreases drastically 21 days after treatment when melatonin is injected directly into the tumor (intratumoral injection), and completely disappears 28 days after treatment.

Figure 4:
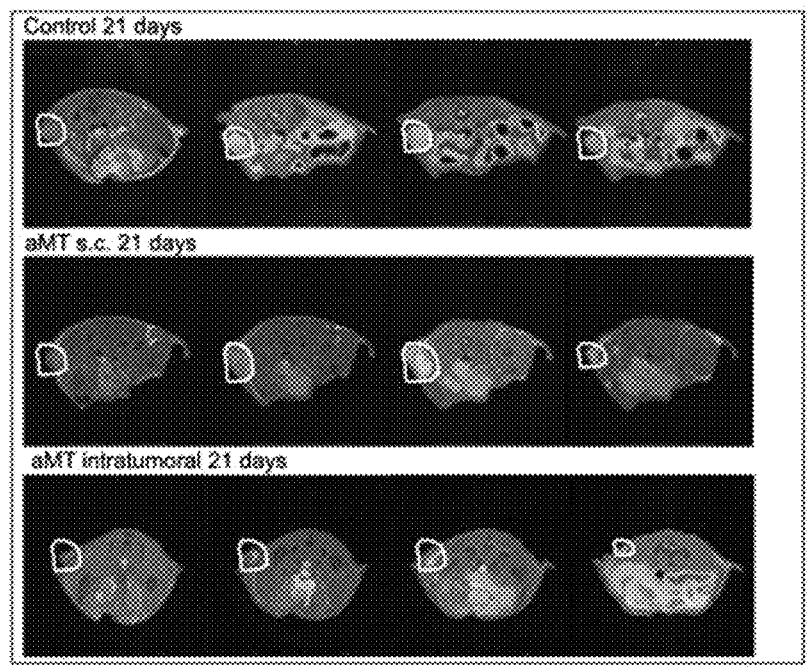
FIG. 4. Analysis of the tumor volume by means of NMR analysis. Tumor size was measured 21 days after treatment. A much denser tumor that is more irrigated is observed in the control. When melatonin reaches the tumor through the systemic route, the tumor volume decreases, although the effect is not very significant. However, when melatonin is administered intratumorally, the decrease in tumor volume is so drastic that the tumor can hardly be observed.
Figure 5:
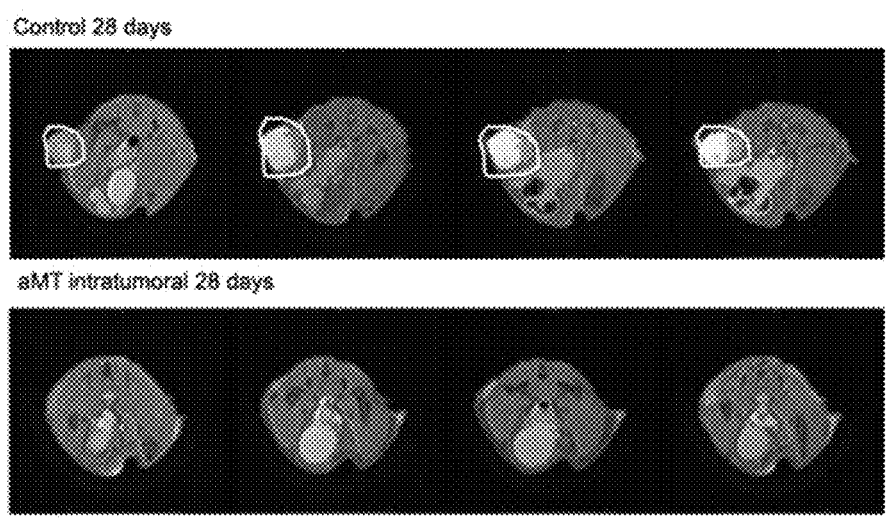
FIG. 5. NMR performed 28 days after treatment. A considerable increase in tumor volume with respect to the 21-day control (preceding diagram) is observed. However, the tumor of the mice treated with intratumorally administered melatonin has virtually disappeared. Hardly any tumor activity is observed.
Figure 6:
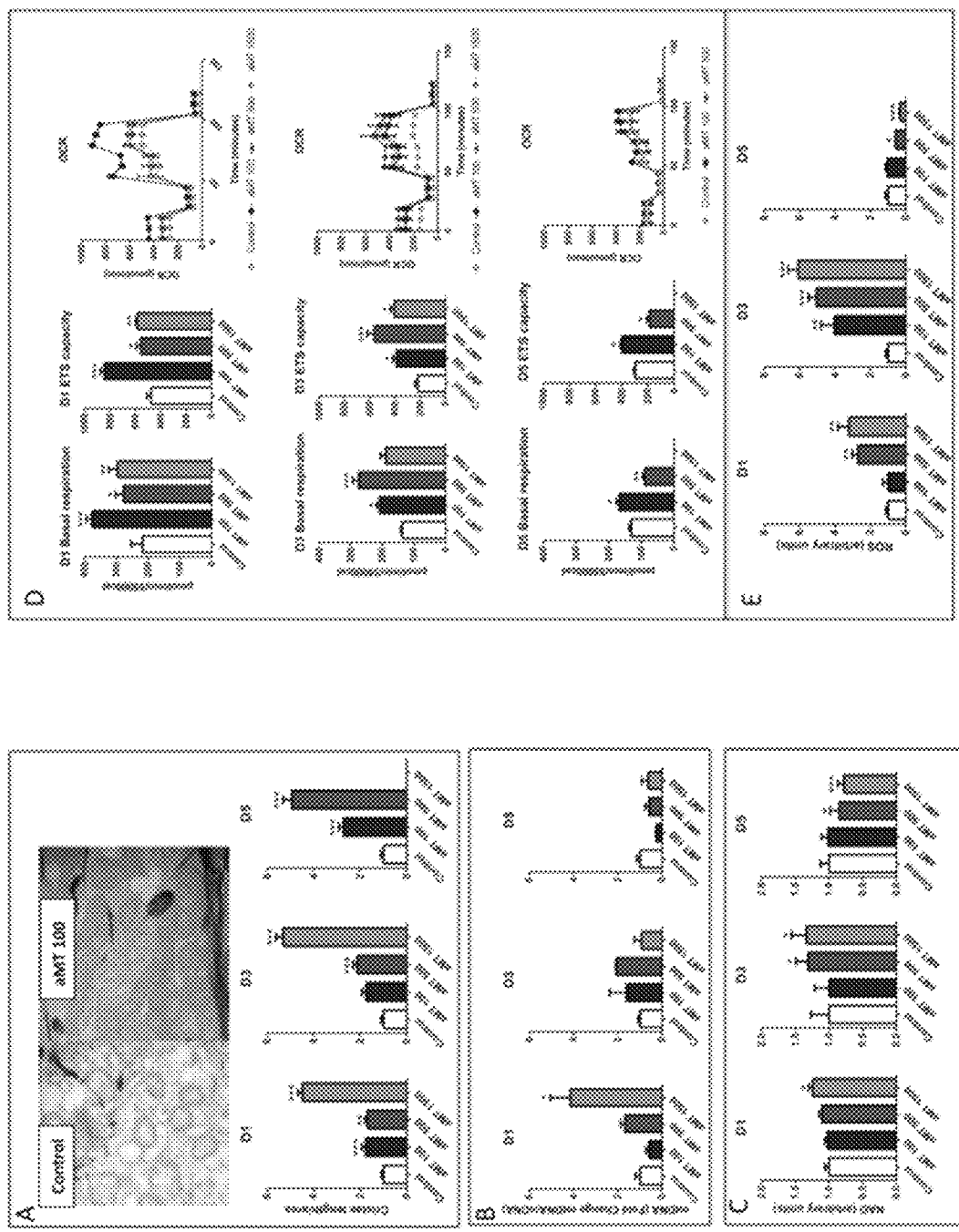
FIG. 6. Mitochondria and cristae analysis. It is observed that melatonin increases the number of mitochondria as well as the number of cristae (FIG. 6A). It also increases mitochondrial DNA (FIG. 6B) and mitochondrial mass (FIG. 6C). The result is an increase in respiratory chain complexes, and accordingly an increase in oxygen consumption (6D), which is related to an increase in free radicals (6E) and oxidative stress. This increase in free radicals induces cell death in tumor cells.
Figure 7:
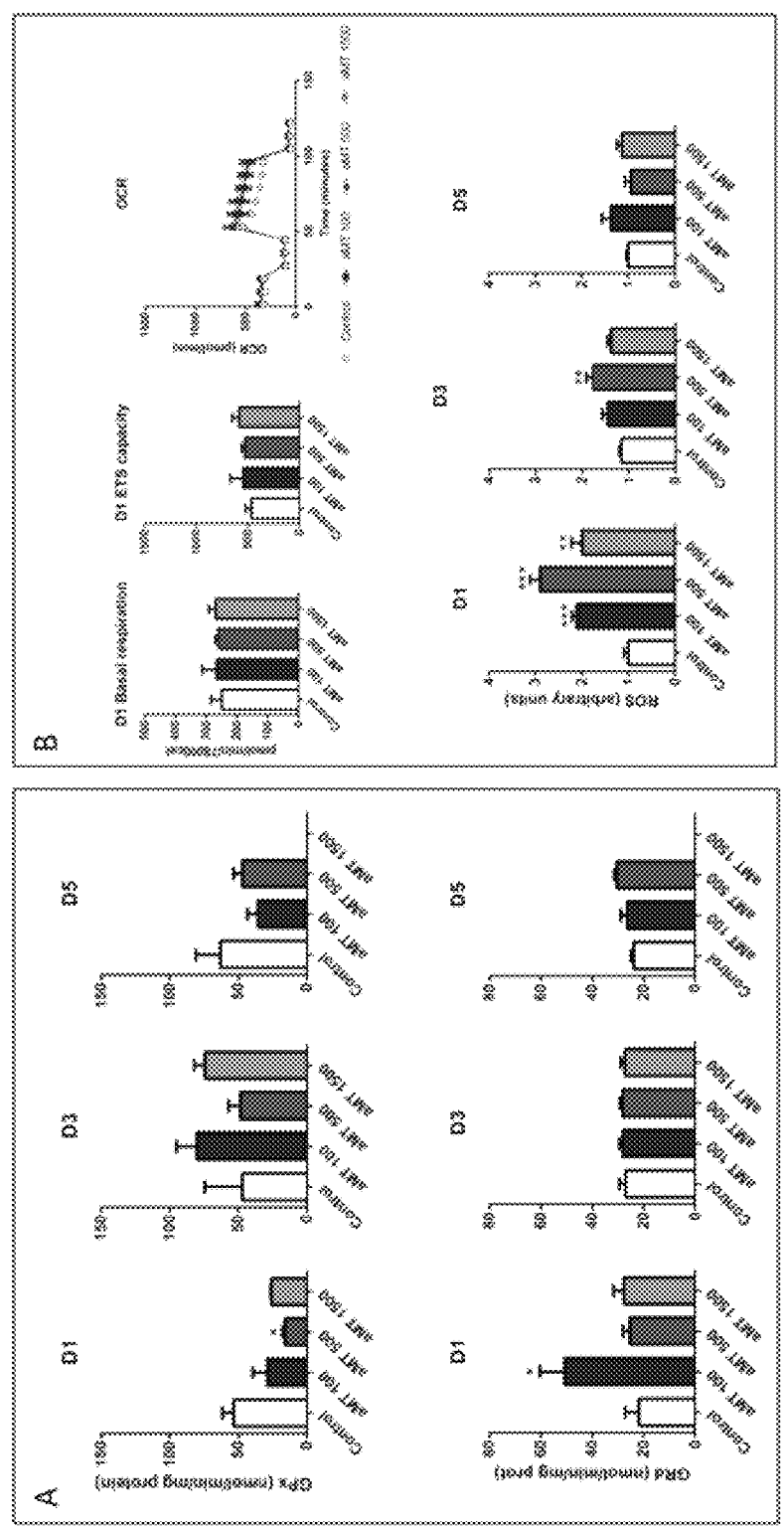
FIG. 7. Study of the GPx and GRd antioxidant enzyme activity in CAL-27 tumor cells. It is observed that melatonin does not increase the activity of these enzymes (7A). However, it is observed that mitochondrial oxygen consumption in SCC-9 cells, and accordingly the production of free radicals (7B), is much lower. Melatonin has lesser effect on these cells because it enters in smaller amounts.

In the NMR images (FIG. 4), certain necrotic areas are observed in the tumors treated with s.c. administered melatonin. By means of NMR analysis, it is observed that the decrease in tumor volume is not as obvious as that observed in the photographs (FIG. 3). However, when melatonin is injected directly into the tumor, a drastic decrease in tumor volume occurs, with the tumor disappearing almost completely 21 days after treatment. After 28 days, the tumor disappears completely, practically without any trace of tumor activity. In contrast, the size of the tumor in the control group increased significantly with respect to the size observed after 21 days and the tumor was invasive (FIG. 5).

The invention claimed is:
1. A method for the treatment of a carcinogenic tumor, which method comprises administering a therapeutically effective amount of a pharmaceutical composition comprising at least one compound of formula X,

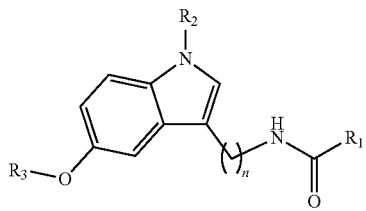

where:
- n is an integer between 1 and 4;
- $R_1$ and $R_3$ are independently selected from the group consisting of linear or branched $C_1$-$C_4$ alkyl;
- $R_2$ is hydrogen, linear or branched $C_1$-$C_4$ alkyl, a —C(=O)O—Ra group or a —C(=O)—N(H)—Ra group, wherein Ra is a linear or branched $C_1$-$C_4$ alkyl group;
- or a salt, solvate, or prodrug thereof,
- wherein the compound of formula X has a concentration of at least 0.1% (w/v) with respect to the total volume of the composition, and wherein a solvate is selected from hydrates and alcoholates.

2. The method according to claim 1, wherein $R_1$ and $R_3$ are independently selected from the group consisting of linear $C_1$-$C_2$ alkyl.

3. The method according to claim 1, wherein $R_1$ and $R_3$ are methyl.

4. The method according to claim 1, wherein compound X is melatonin.

5. The method according to claim 1, wherein the concentration of compound X is at least 0.3% (w/v) with respect to the total volume of the composition.

6. The method according to claim 1, wherein the concentration of compound X is less than 5% (w/v) with respect to the total volume of the composition.

7. The method according to claim 1, wherein said composition can be administered intratumorally.

8. The method according to claim 1, wherein the composition is injectable.

9. The method according to claim 1, wherein the concentration of compound X is 0.3% (w/v) with respect to the total volume of the composition.

10. The method according to claim 1, wherein the tumor is a solid tumor.

11. The method according to claim 1, wherein the tumor is selected from the group consisting of tumors associated with head and neck cancer, melanoma, breast tumors, ocular tumors, urologic tumors, hepatic tumors, cervical tumors, lymphomas, thyroid tumors, and soft part sarcoma.

12. The method according to claim 1, wherein the composition further comprises a pharmaceutically acceptable vehicle.

13. The method according to claim 1, wherein the composition further comprises another additional active ingredient.

14. The method according to claim 12, wherein said second active ingredient is an anti-tumor active ingredient.

* * * * *